United States Patent [19]

Jackowski

[11] Patent Number: 4,920,980
[45] Date of Patent: May 1, 1990

[54] CATHETER WITH CONTROLLABLE TIP

[75] Inventor: Stefan A. Jackowski, Hollywood, Fla.

[73] Assignee: Cordis Corporation, Miami Lakes, Fla.

[21] Appl. No.: 95,997

[22] Filed: Sep. 14, 1987

[51] Int. Cl.$^5$ ............................................. A61N 1/05
[52] U.S. Cl. .................... 128/786; 128/658; 128/642; 604/95
[58] Field of Search .............. 128/786, 658, 639, 772, 128/642, 657; 604/95

[56] References Cited

U.S. PATENT DOCUMENTS

| | | | |
|---|---|---|---|
| 3,470,876 | 10/1969 | Barchilon | 604/95 |
| 3,485,234 | 12/1969 | Stevens . | |
| 4,409,993 | 10/1983 | Furihata | 128/784 |
| 4,456,017 | 6/1984 | Miles | 604/95 |
| 4,586,932 | 5/1986 | Gould et al. | 604/95 |
| 4,677,990 | 7/1987 | Neubauer | 128/786 |

FOREIGN PATENT DOCUMENTS 8801885  3/1988  PCT Int'l Appl. ............ 604/95

OTHER PUBLICATIONS

Brochure of Cordis Corporation 1984—Cordis Ducor Lumelec Electrode Catheters—An Indispensable Tool for the Safe and Quick Assessment of Cardiac Function (1 page).

Primary Examiner—Edward M. Coven
Assistant Examiner—Jessica J. Harrison
Attorney, Agent, or Firm—Gerstman & Ellis, Ltd.

[57] ABSTRACT

In a catheter which comprises a tubular body having a bore, a wire member is loosely positioned in the bore. The wire member is secured to the catheter at a position adjacent the distal end, such position being radially spaced from the axis of the catheter. The wire member extends through the bore and out of the proximal end of the catheter, so that the distal end of the catheter can be bent by pulling the wire member. The wire member may also be connected at the distal end of the catheter to an electrode, so that the wire member serves both as a bending control member and as the means for electrical connection with the electrode.

23 Claims, 1 Drawing Sheet

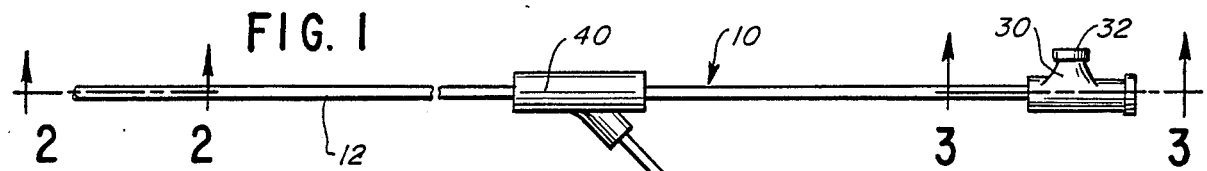
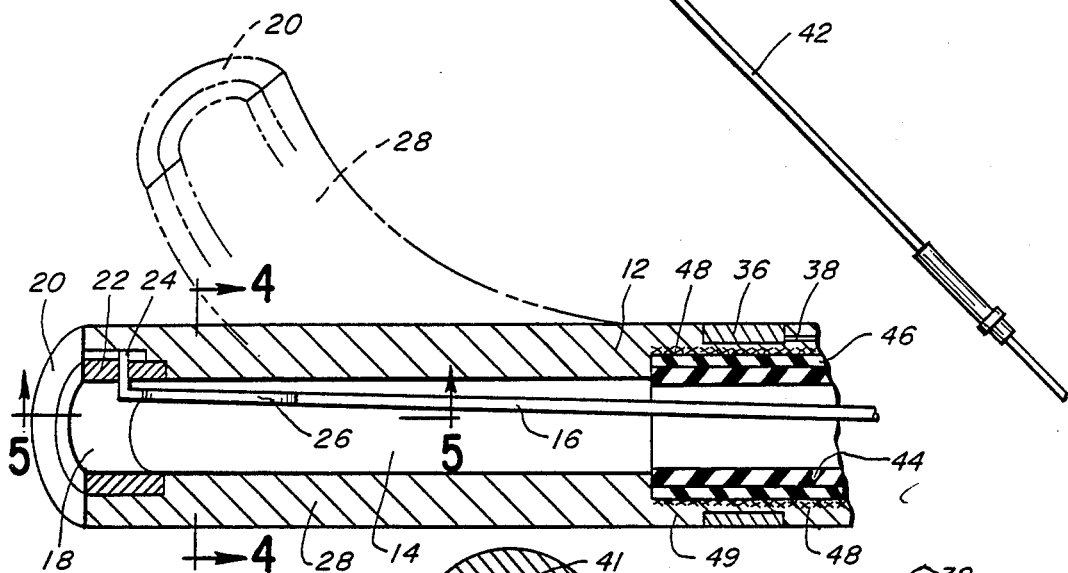
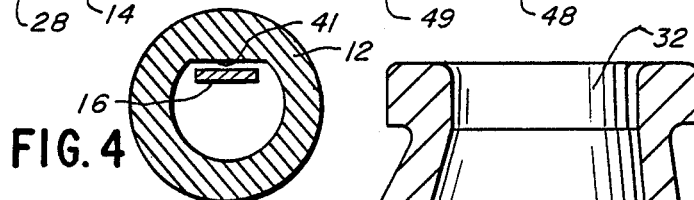
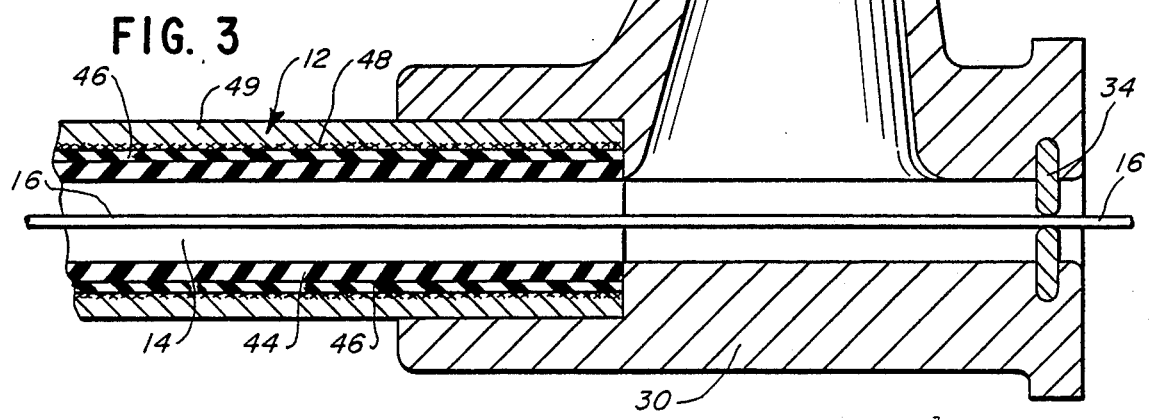
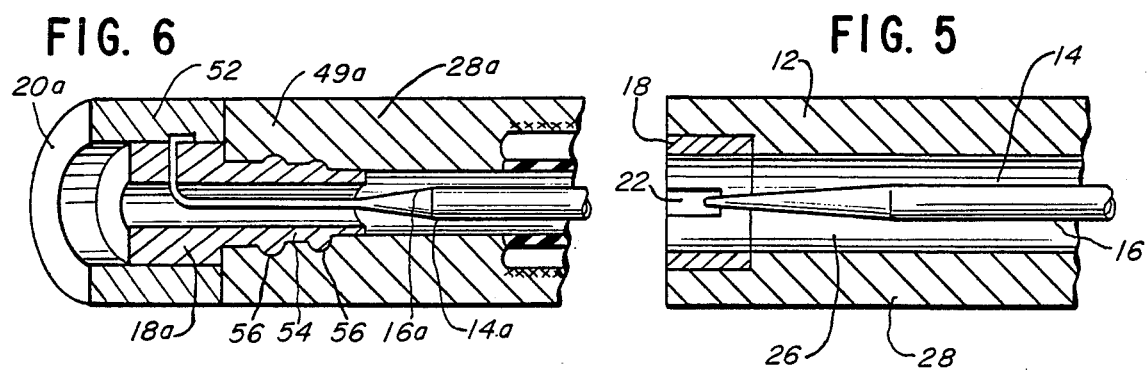

CATHETER WITH CONTROLLABLE TIP

BACKGROUND OF THE INVENTION

Catheters for insertion through a blood vessel in the heart, and other catheters as well, are in very common medical use. When such a catheter is inserted into a blood vessel, it has to follow the irregularly shaped path defined by the blood vessel until the distal end of the catheter reaches the desired location in the heart or elsewhere.

To assist in this purpose, some catheters have been previously formed with a curved distal end. A guide wire may be inserted into the bore or lumen of the catheter, thereby straightening out the preformed curve. For example, the guide wire may be positioned to reduce the curve of the distal end of the catheter when placing the catheter into the atrium of the heart. However, some curvature is required to allow passage of the catheter through the heart valve, and this can be provided in prior art catheters by retraction of the guide wire. For known suction/ablation catheters, location of a desired conduction pathway in the heart is generally accomplished as well while the catheter is in its curved configuration with the guide wire retracted or removed. If the prior art catheters need to be straightened at their distal ends again, the guide wire may be once again advanced.

There is a present need for greater freedom of motion of catheter tips in some medical procedures, above and beyond that which can be currently provided in catheters having preformed tips at their distal ends, which tips may be straightened out by means of a guide wire. For example, in suction/ablation catheters, when one is mapping the conduction pathways or site of origin of abnormal electrical activity in the heart, greater flexibility of the curved, preformed tips of prior art catheters would be desired. At the present time, manipulation of the guide wire is often necessary to permit the curve to assume its shape and then to straighten it out again as the mapping takes place. However, it may be desired for the curved tip to assume a different shape than the curve that is preformed into a prior art catheter, with a curve that is either greater or lesser than the preformed curve, but not straight.

In accordance with this invention, a catheter is provided in which the physician-user can manipulate the curvature of its distal end, in a single plane, over a predetermined arc of variable positions. Such a catheter, for example, could be used for locating, mapping, and ablating abnormal conduction tissue in the heart with less manipulation and more assurance of good performance. It also may be used with advantage for many other purposes.

Additionally, the catheter of this invention more easily follows the contours of the ventricle of the heart, for example, for better positioning of an electrode for desired ablation of a portion of cardiac muscle containing an abnormal conduction pathway. The improved variable curvature of the distal end of a catheter of this invention facilitates this purpose, and also any of the large variety of medical or any other desired procedures involving a catheter or a structural equivalent thereto.

DESCRIPTION OF THE INVENTION

In this invention, a catheter is provided which comprises a tubular body having a bore and having proximal and distal ends. By the improvement of this invention, a wire member is loosely positioned in the bore, the wire member being secured to the catheter adjacent the distal end at a position which is radially spaced from the axis of the catheter, that is, the longitudinal centerline of the catheter. The wire member extends through the bore and out of the proximal end of the catheter. As a result of this, the distal end of the catheter can be temporarily bent by pulling the wire member. Typically, upon release of or pushing of the wire member, the catheter can move back into substantially straight configuration.

Preferably, the wire member may be relatively flattened and also preferably tapered in an area adjacent the position to which the wire member is secured to the catheter. The effect of this is to improve control of the direction of bending, which direction will be essentially perpendicular to the plane of the flattened area.

The catheter may carry an electrode adjacent its distal end, with the wire member being secured at the electrode. In this circumstance, the wire member can perform a double function: first it can be used to control the curvature of the catheter tip, but also the wire may be electrically conductive and electrically connected to the electrode, to serve as the conduit for the transfer of signals or other electrical impulses to and from the electrode.

The catheter may also carry a second electrode, for example a ring electrode, at a position spaced from the distal end, as is conventional.

Likewise, the proximal end of the catheter may carry a connector for providing fluid flow connection between the catheter bore and a flow conduit. Additionally, the proximal end may carry a sliding, dynamic seal which permits the wire member to pass out of the proximal end while preventing fluid leakage.

Accordingly, the wire member may be attached to a combined electrical sensing apparatus and pulling member. When the wire member is pulled in a proximal direction relative to the catheter, the distal tip of the catheter will form a curve in a direction which may be predetermined, particularly by the use of the relatively flattened and tapered wire member portion as described above. The radius of curvature of the curved portion may be varied in accordance with the amount that the wire member is pulled rearwardly in the proximal direction, or, when and as desired, the catheter may be substantially straightened out again by releasing of the wire member from rearward tension, and pushing the wire distally if necessary. At the same time, through all of this, electrical impulses may be sent and received along the wire member for communication with the distal electrode.

Apart from that, the catheters of this invention may be of conventional construction for the particular use to which it is desired to be put.

DESCRIPTION OF DRAWINGS

In the drawings,

FIG. 1 is a plan view of a catheter in accordance with this invention;

FIG. 2 is a sectional view taken along line 2—2 of FIG. 1;

FIG. 3 is a sectional view taken along line 3—3 of FIG. 1;

FIG. 4 is a sectional view taken along line 4—4 of FIG. 2.

FIG. 5 is a longitudinal sectional view similar to FIG. 2, but rotated 90 degrees about the longitudinal axis of said catheter; and FIG. 6 is a sectional view similar to FIG. 2 of a modified embodiment.

DESCRIPTION OF SPECIFIC EMBODIMENTS

Referring to FIGS. 1 through 4, a single axis steerable suction/ablation catheter is disclosed, modified in accordance with this invention. Suction/ablation catheters are utilized to permanently destroy conduction pathways in the heart, when such a conduction pathway is exhibiting sufficient abnormal activity to endanger the patient's health. The targeted pathway is generally located by bipolar recording of the electrical activity generated by the pathway, and then changing to unipolar recording for the definitive location. Suction is then applied to cause the distal end of the catheter to adhere to the cardiac muscle portion containing the conduction pathway by sucking such muscle portion a small distance into the lumen of the catheter tip. By this, the catheter is stabilized. Then, a typically direct current shock is applied to the tissue within and adjacent the lumen, thereby destroying the pathway. The desired destruction is confirmed by the loss of electrical activity distal to the site of delivery of the direct current shock.

The invention of this application provides an added capability to the illustrated catheter to facilitate the best possible positioning of the catheter prior to application of the direct current shock. The variable curvature of the distal end of the catheter of this invention contributes significantly to ease and effectiveness of use.

Catheter 10 comprises a tubular body 12 defining a lumen or bore 14. As shown in FIGS. 2 and 3, wire member 16 is loosely positioned in bore 14. Tubular electrode 18 is positioned adjacent distal end 20 of the catheter, with bore 14 being open to the distal end as shown in FIG. 2. Tubular electrode 18 defines a slot 22 in a portion of its length, to permit curved distal tip 24 of wire member 16 to hook into electrical contact with electrode 18, being typically soldered in place.

Typically, as particularly shown in FIGS. 2 and 4, end portion 26 of wire member 16 is tapered and flattened. This helps to direct the tip portion 28 of catheter 10 into a predetermined direction of bending which is generally perpendicular to the plane of flattened end 26.

At the proximal end of catheter 10, connector 30 is provided, defining a side port 32 for sealing fluid flow connection between catheter bore 14 and a flow conduit which can connect to side port 32. Additionally sealing member 34 is typically provided through which wire member 16 extends in slidable, sealing relation therewith, so that wire member 16 may be moved back and forth to a degree without significant leakage of fluid from the interior of the catheter. Antirotation lock means may be provided to prevent rotation of wire member 16 to avoid spiraling or twisting thereof.

Accordingly, during use of the catheter, it may be inserted into a vein of the patient with distal tip 28 being in straight configuration. However, when it is necessary for further advancement of the catheter, wire member 16 may be pulled relative to the rest of the catheter, to impose upon distal end 28 of the catheter a curved configuration as shown in phantom lines in FIG. 2. The degree of such curvature is of course dependent upon the distance that wire member 16 is pulled rearwardly, so that the user of the catheter can know what the degree of curvature of tip 28 is, on a moment by moment basis, as the catheter is advanced into the heart, and as the process of locating and mapping the abnormally functioning conduction tissue proceeds. Likewise, the variable curvature of distal tip 28 in accordance with this invention facilitates the precise placement of distal end 20 of catheter 10 at exactly the proper location.

Following this, as is conventional, suction may be provided through port 32 to cause the heart tissue to move into bore 14 from distal end 20, and to cause distal tip 28 to temporarily adhere to such tissue by suction.

Up to this point, electrode 18 may be used for sensing, with the electrical connection between electrode and conventional sensing apparatus being made through wire member 16. When it is desired to provide the pulse of tissue inactivating current, that may be also provided to electrode 18 through wire member 16, which thus provides a double function.

When it is desired to straighten out distal tip 28, the rearward tension on wire member 16 may be released, and it may be pushed forward, if desired, to cause substantial straightening out of the curved distal tip 28 back toward a straight configuration.

If desired, wire member 16 may be not for electrical connection, but instead, a conventional electrical wire may be embedded in the wall of tubular body 12 in electrical communication with electrode 18.

A second ring electrode 36 may also be provided, connected to electric wire 38. Electric wire 38 is embedded in the wall of tubular body 12 until it reaches intermediate connector 40, which may be of conventional design. There, electric wire 38 branches off into branch line 42, which may also be of conventional design, and for connection with conventional electrical sensing equipment. Any added electrical wire communicating from electrode 18 and embedded in the wall of tubular body 12 may also branch off into branch line 42 at intermediate connector 40 in the same manner.

It may be desirable for a proximal portion of catheter 10, spaced from end 20 by distal end portion 28, to carry a tubular liner 44 as shown which may be made of a lubricating material such as polytetrafluoroethylene, to facilitate the retraction and subsequent advancement of wire member 16. Surrounding tubular member 44 there may be a tubular stiffening member 46, to provide a desired degree of stiffness to catheter 10, if desired. Stiffening sleeve 46 may be made, for example, out of a polycarbonate material.

Outside of tubular member 46, one may add a tubular layer of stainless steel braiding 48, as in conventionally applied to provide rotational stiffness or torque control to the catheter, so that the distal end 28 may be rotated by manipulation of the proximal end thereof, for example by rotating either of connectors 30 or 40. On top of this, a layer 49 of appropriate plastic material such as polyurethane may be added by extrusion or the like to complete the structure of tubular body 12.

It can be seen that none of layers 44, 46, or 48 extend into the area of distal tip 28, which is substantially exclusively made of the polyurethane coating plastic. Thus, distal tip 28 is much more flexible and bendable than the remainder of the catheter, for ease of bending distal tip 28 by means of pull wire 16 in the manner previously described. Additionally, the softened tip reduces the possibility of damage to heart tissue as the catheter is advanced and manipulated.

It may be desired for tubular electrode 36 to be welded, soldered, or brazed to stainless steel braiding 48, to establish electrical connection with the braid. If desired, electrical signals may communicate to and from electrode 36 through stainless steel braiding 48 rather than through wire 38, with electrical communication between branch line 42 and braiding 48 being provided within intermediate connector 40. Braiding 48 may also act as an electrical shield for conductor-control wire 16.

Electrode 18 is shown to be in substantially flush or recessed relation with distal end 20. Electrode 18 may be made in conventional manner of an alloy of tungsten and rhenium.

The bore 14 of catheter 10 may be cylindrical along most of its length, but adjacent distal end 20 it may be of D-shaped cross section having flat side 41 adjacent to and parallel to flattened portion 26 of wire member 16. This helps fix the direction of bending of tip 28.

In operation, the suction/ablation catheter as described herein is positioned in the ventricle of the heart through an appropriate vein. Side port 32 of connector 30 is coupled to a manifold which, in turn, is coupled to a saline infusion set and a suction device so that suction may be applied and saline solution administered as appropriate, without disconnecting the catheter.

A conventional switch box may be utilized, to which a conventional external cardiac pacer, recording equipment, and a defibrillator (as a source of direct current shock) are coupled. Both branch line 42 and wire member 16 are then coupled to the switch box for electrical connection with and control of both electrodes 18 and 34.

The conduction path is located by mapping, utilizing the catheter as a bipolar lead, with both tip electrode 18 and ring electrode 36 being used. One may manipulate the conductor-control wire 16 by putting tension on or compressing it, to cause distal end 28 to form an arc of the desired radious of curvature, or to straighten out, as may be desired. When the abnormal conduction pathway in the heart has been crudely located, the catheter may be utilized as a unipolar lead with the tip electrode 18 functioning as the active electrode and an electrode pad on the patient's chest wall serving as the reference electrode. Again, distal tip portion 28 can be moved into an arc of variable curvature by pulling or compressing conductor-control wire 16. Once the pathway is found, suction may be applied through side port 32, stabilizing the catheter tip and drawing a portion of the heart tissue containing the pathway into bore 14 thereof. Then, a preferably direct current shock is applied through electrode 18 to destroy the pathway and interrupt conduction.

Referring to FIG. 6, a modified design for the distal tip 28a catheter is disclosed. Apart from the modifications shown, the design an purpose of the catheter may be identical to that of the previous embodiment.

Conductor-control wire 16a fits loosely in lumen or bore 14a of the catheter and is secured into electrically conductive relation with distal electrode 18a. As one modification of this structure, the polyurethane or other plastic coating 49a which is applied may terminate short of distal end 20a of the catheter. The actual distal end 20a is then defined by a tubular, refractory, insulating member 52 which is typically made of a ceramic capable of withstanding high electrode temperatures. Thus, the distal end of the catheter does not deteriorate despite repeated use of electrode 18a in providing substantial direct current shock to destroy abnormal conduction pathways in the heart.

Additionally, electrode 18a may be recessed as illustrated. Electrode 18a also defines a projecting proximal end 54 carrying annular ribs 56, for a frictional retention connection with body of plastic material 49a.

Control wires 16, 16a may be made of stainless steel, and may, for example have a diameter of 0.018 inch. Flat tapered area 26 acts as a leaf spring to provide improved performance in accordance with this invention.

The above has been offered for illustrative purposes only, and is not intended to limit the scope of the invention of this application, which is as defined in the claims below.

That which is claimed is:

1. In a catheter which comprises a tubular body having a bore and having proximal and distal ends, said catheter carrying an electrode adjacent said distal end, the improvement comprising, in combination:

a wire member loosely positioned in said bore, said wire member being secured to said catheter at said electrode at a position adjacent said distal end, said position being radially spaced from the axis of said catheter, said wire member extending through said bore and out of the proximal end of said catheter, whereby the distal end of said catheter is temporarily bent by pulling said wire member, and wherein said wire member is flattened and tapered relative to the rest of the wire member in an area adjacent said position, to improve control of the direction of bending.

2. The catheter of claim 1 in which the bore of the tubular body adjacent said distal end is of D-shaped cross section, with the plane of said flattened area being substantially parallel to the flat side of said D-shaped cross section.

3. In a catheter which comprises a tubular body having a bore and having proximal and distal ends, said catheter carrying and electrode adjacent said distal end, the improvement comprising, in combination:

a wire member loosely positioned in said bore, said wire member being secured to said catheter at said electrode at a position adjacent said distal end, said position being radially spaced from the axis of said catheter, said wire member extending through said bore and out of the proximal end of said catheter, whereby the distal end of said catheter is temporarily bent by pulling said wire member, and wherein said wire member is electrically conductive and electrically connected said electrode.

4. The catheter of claim 2 in which a second electrode is carried by said catheter at a position spaced from said distal end.

5. The catheter of claim 3 in which said proximal end carries sliding seal means for said wire member.

6. The catheter of claim 5 in which said proximal end carries a connector for providing fluid flow connection between said catheter bore and a flow conduit.

7. In a catheter which comprises a tubular body having a bore and having proximal and distal ends, the improvement comprising, in combination:

a wire member loosely positioned in said bore, an electrode carried by said catheter adjacent said distal end, said wire member being connected to said electrode at a position which is radially spaced from the axis of said catheter, said wire member defining a flattened area relative to the rest of the wire member, said flattened area being positioned adjacent said position of electrode connection, said wire member extending through said bore and out of the proximal end of said catheter, whereby the distal end of said catheter is temporarily bent by pulling said wire member, and a second electrode carried by said catheter at a position spaced from said distal end.

8. The catheter of claim 7 in which said wire member is electrically conductive and electrically connected to said electrode.

9. The catheter of claim 8 in which said proximal end carries sliding seal means for said wire member.

10. The catheter of claim 8 in which said proximal end carries a connector for providing fluid flow connection between the catheter bore and a flow conduit.

11. The catheter of claim 8 in which the bore of the tubular body adjacent said distal end is of D-shaped cross section, with the plane of said relatively flattened area being substantially parallel to the flat side of said D-shaped cross section.

12. The catheter of claim 7 in which the bore of the tubular body adjacent said distal end is of D-shaped cross section, with the plane of said flattened area of the wire member being substantially parallel to the flat side of said D-shaped cross section.

13. In a catheter which comprises a tubular body having a tubular inner wall defining a bore and having proximal and distal ends, the improvement comprising, in combination:
a wire member loosely positioned in said bore, said wire member being laterally secured to said inner wall at a positioned adjacent said distal end, said position being radially spaced from the axis of said catheter, said wire member extending through said bore and out of the proximal end of said catheter, whereby the distal end of said catheter is temporarily bent by pulling said wire member, and wherein said wire member is relatively flattened and tapered in an area adjacent said position, to improve control of the direction of bending.

14. The catheter of claim 13 in which said proximal end carries sliding seal means for said wire member.

15. The catheter of claim 14 in which said proximal end carries a connector for providing fluid flow connection between said catheter bore and a flow conduit.

16. In a catheter which comprises a tubular body having a tubular inner wall defining a bore and having proximal and distal end, the improvement comprising, in combination:
a wire member loosely positioned in said bore, said wire member being laterally secured to said inner wall at a position adjacent said distal end, said position being radially spaced from the axis of said catheter, said wire member extending through said bore and out of the proximal end of said catheter, whereby the distal end of said catheter is temporarily bent by pulling said wire member;
said wire member is flattened in an area adjacent said position, to improve control of the direction of bending, the bore of the tubular body adjacent said distal end being of D-shaped cross section, with the plane of said flattened area being substantially parallel to the flat side of side D-shaped cross section.

17. In a catheter which comprises a tubular body having a tubular inner wall defining a bore having proximal and distal open ends, the improvement comprising, in combination:
a wire member loosely positioned in said bore, said wire member being laterally secured to said tubular inner wall at a position adjacent said distal end, said position being radially spaced from the axis of said catheter, said wire member extending through said bore and out of the proximal end of said catheter, whereby the distal end of said catheter is temporarily bent by pulling said wire member, said catheter being free of any internal, helical spring member, said tubular inner wall is generally flexible except for a rigid wall portion to which said wire is secured, and wherein said wire member is relatively flattened and tapered in an area adjacent said position, to improve control of the direction of bending.

18. In a catheter which comprises a tubular body having a tubular inner wall defining a bore having proximal and distal open ends, the improvement comprising, in combination:
a wire member loosely positioned in said bore, said wire member being laterally secured to said tubular inner wall at a position adjacent said distal end, said position being radially spaced from the axis of said catheter, said wire member extending through said bore and out of the proximal end of said catheter, whereby the distal end of said catheter is temporarily bent by pulling said wire member, said catheter being free of any internal, helical spring member; and said wire member is flattened, the bore of the tubular body adjacent said distal end being of D-shaped cross section, with the plane of said flattened area being substantially parallel to the flat side of said D-shaped cross section.

19. A catheter which comprises:
a tubular body having proximal and distal ends;
said tubular body having a tubular inner wall defining a bore;
a wire member loosely positioned in said bore;
anchoring means within said tubular inner wall securing said wire member to said tubular inner wall adjacent said distal end at a location that is laterally spaced from the central axis of the bore;
said wire member extending through the bore and out of the proximal end of the catheter, whereby the distal end of the catheter is temporarily bent by pulling the wire member.

20. A catheter as defined by claim 19 in which the distal end is open to provide a suction/ablation catheter.

21. A catheter as defined by claim 19 in which the tubular body defines a slot for receiving the wire member.

22. A catheter as defined by claim 19 in which the wire member is relatively flattened and tapered in an area adjacent said location, to improve control of the direction of bending.

23. A catheter as defined by claim 19 in which the wire member has an angled end portion which extends laterally into the tubular inner wall to be secured to the tubular inner wall.

* * * * *